(12) United States Patent
Joos et al.

(10) Patent No.: US 9,758,264 B2
(45) Date of Patent: Sep. 12, 2017

(54) FILLING AND CLOSING DEVICE, AND METHOD FOR FILLING AND CLOSING AN APPLICATOR FOR ACTIVE SUBSTANCES

(71) Applicant: Harro Höfliger Verpackungsmaschinen GmbH, Allmersbach im Tal (DE)

(72) Inventors: Thomas Joos, Gschwend (DE); Achim Götz, Winnenden (DE); Markus Bohn, Stuttgart (DE); Udo Mattern, Emmetten (CH); Claudia Mattern, Emmetten (CH)

(73) Assignee: Harro Höfliger Verpackungsmaschinen GmbH, Allmersbach im Tal (DE)

( * ) Notice: Subject to any disclaimer, the term of this patent is extended or adjusted under 35 U.S.C. 154(b) by 422 days.

(21) Appl. No.: 14/377,669

(22) PCT Filed: Feb. 6, 2013

(86) PCT No.: PCT/EP2013/000360
§ 371 (c)(1),
(2) Date: Aug. 8, 2014

(87) PCT Pub. No.: WO2013/117333
PCT Pub. Date: Aug. 15, 2013

(65) Prior Publication Data
US 2015/0013828 A1  Jan. 15, 2015

(30) Foreign Application Priority Data
Feb. 10, 2012  (EP) .................................... 12000863

(51) Int. Cl.
*B65B 43/54* (2006.01)
*B65B 7/26* (2006.01)
(Continued)

(52) U.S. Cl.
CPC ............... *B65B 3/003* (2013.01); *B65B 7/26* (2013.01); *B65B 43/54* (2013.01); *B65B 51/14* (2013.01); *A61M 15/0028* (2013.01)

(58) Field of Classification Search
CPC  B65B 3/003; B65B 7/26; B65B 43/54; B65B 51/14; A61M 15/0028
(Continued)

(56) References Cited

U.S. PATENT DOCUMENTS 5,215,221 A  6/1993  Dirksing

FOREIGN PATENT DOCUMENTS

EM  001 790 908-0001  8/2010
EP  2 048 083 A1  4/2009

*Primary Examiner* — Robert Long
*Assistant Examiner* — Xavier A Madison
(74) *Attorney, Agent, or Firm* — Gudrun E. Huckett

(57) ABSTRACT

The invention relates to a filling and closing device (20) for an applicator for active substances (1) and to a method for filling and closing such an applicator for active substances (1) by means of such a filling and closing device (20). The applicator for active substances (1) comprises an applicator tube (7) that overlaps the sealing edge (5), at least in part. The filling and closing device (20) comprises a receiving element (21) for the lower part (2) of the applicator for active substances (1), having a circumferential pressure surface (22) and a receiving channel (23) for the applicator tube (7), said receiving channel extending below the pressure surface (22). The receiving element (21) is constructed of at least two parts, having a base element (24) and a cover element (25) that is movable with respect to the base element (24). After completion of the filling and sealing process, the cover element (25) is moved relative to the base element (24), such that the receiving channel (23) formed therebetween is exposed. The filled and sealed applicator for active (Continued)

substances (1) can then be easily removed from the receiving element (21) by way of the applicator tube (7).

9 Claims, 4 Drawing Sheets

(51) Int. Cl.
    *B65B 51/14*     (2006.01)
    *B65B 3/00*     (2006.01)
    *A61M 15/00*     (2006.01)

(58) Field of Classification Search
    USPC ........ 141/2, 18; 53/467, 473, 173, 563, 237,
                                      53/240, 249; 401/132
    See application file for complete search history.

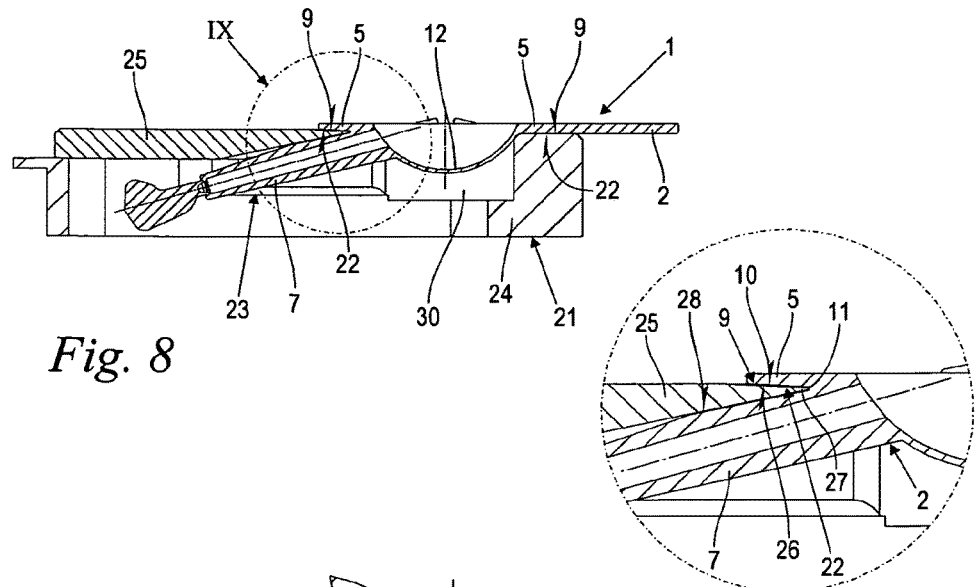
Fig. 8
Fig. 9
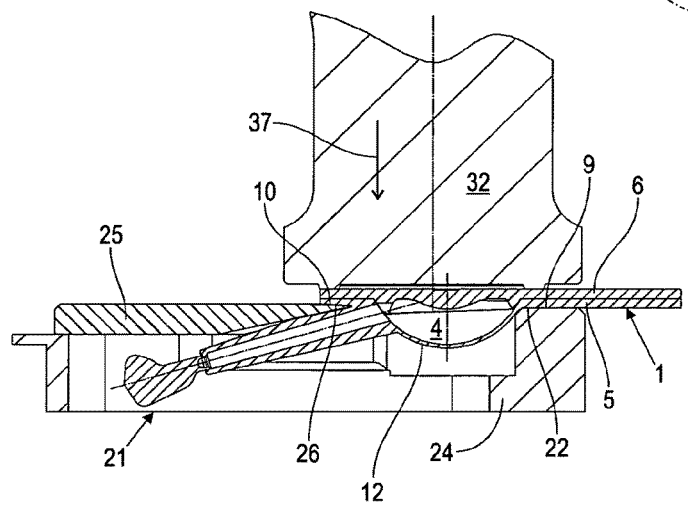
Fig. 10
Fig. 11
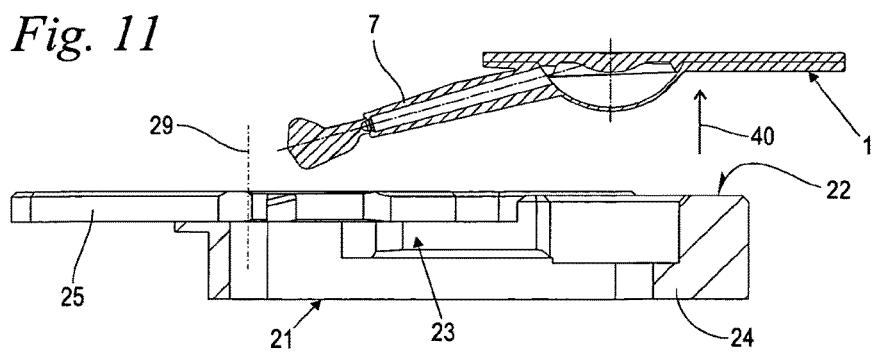

FILLING AND CLOSING DEVICE, AND METHOD FOR FILLING AND CLOSING AN APPLICATOR FOR ACTIVE SUBSTANCES

BACKGROUND OF THE INVENTION

The invention concerns a filling and closing device as well as a method for filling and closing an applicator for active substances.

For certain active substance preparations for the human body, a precise dosage is required. In order to ensure such a precise dosage by the user, dosage units are provided which contain the predetermined quantity of the active substance preparation and which administer, when applied, precisely the predetermined quantity to the human body. Moreover, active substance applicators are also known that are provided for single use and in this context have a dual function. On the one hand, they contain a fixedly predetermined dosage quantity of the active substance preparation. On the other hand, they not only serve for providing but also for administering the active substance preparation in the desired quantity to the desired location. After completed application, the empty unit is disposed of. Such an active substance applicator for providing and administering a single dosage into the nose is disclosed in the registered community design 001790908-0001.

The aforementioned active substance applicator has a bottom part and a top part between which a receiving space for an active substance preparation is formed. The bottom part and the top part each have a circumferentially extending sealing rim for seal-tight connection of the top part with the bottom part. The bottom part is provided with an application tube that opens into the receiving space by means of an inner mouth. Relative to the plane of the joined sealing rims, the application tube to be introduced into the nose projects, beginning at the receiving space, at a flat angle past the sealing rims and covers thereby a support surface section of the sealing rim of the bottom part.

A plastic blank for forming the active substance applicator can be produced inexpensively under conditions of mass production as an injection-molded part.

Filling and closing of this plastic bank is however difficult because of the geometric arrangement of the application tube. For filling, a precise positioning of the still open blank is required but the application tube is in the way. For the subsequent closing process in which the top part must be sealed onto the bottom part with the application tube, on the sealing rim of the bottom part a counter pressure must be applied which extends across the entire sealing surface. Only in this way a circumferentially effective, hermetically closed sealing action can be produced. In the area of the application tube, the sealing rim is covered however by the tube so that here access to the sealing rim for application of the counter pressure is not possible.

The object of the invention is to provide a filling and closing device for the aforementioned active substance applicator by means of which a precise positioning, filling, a reliably seal-tight sealing action, and an automated removal of the finished active substance applicator are possible.

SUMMARY OF THE INVENTION

This object is solved by a filling and closing device for an active substance applicator, wherein the active substance applicator comprises a bottom part and a top part, between which a receiving space for an active substance preparation is formed, wherein the bottom part and the top part each have a circumferentially extending sealing rim for seal-tight connection of the top part with the bottom part, wherein the bottom part is provided with an application tube which opens into the receiving space by means of an inner mouth, wherein the sealing rim of the bottom part on its bottom side which is facing away from the top part forms a circumferentially extending support surface, wherein the application tube extends across the sealing rim relative to its plane at least partially in such a way that the circumferentially extending support surface has a support surface section that is at least partially covered by the application tube, wherein the filling and closing device has a receiving element for the bottom part of the active substance applicator with a circumferentially extending pressure surface for contacting the support surface of the bottom part as well as with a receiving channel for the application tube of the bottom part that extends underneath the pressure surface, wherein the receiving element is of an at least two-part configuration with a base element and a cover element which is movable relative to the base element, wherein the receiving channel is formed between the base element and the cover element, wherein the circumferentially extending pressure surface extends across the base element and the cover element such that on the topside of the cover element that is opposite the receiving channel a pressure surface section for contacting the covered support surface section of the active substance applicator is formed.

The invention has further the object to provide a method for filling and closing the aforementioned active substance applicator which ensures a reliable seal-tight sealing action for a high number of cycles.

This object is solved by a method for filling and closing an active substance applicator by means of a filling and closing device according to the invention, comprising the following method steps:

the bottom part of the active substance applicator is inserted such into the receiving element of the filling and closing device that the application tube projects into the receiving channel, wherein the circumferentially extending support surface is resting on the circumferentially extending pressure surface and the covered support surface section on the pressure surface section of the cover element;

the receiving space bulge of the bottom part of the active substance applicator is filled with the active substance preparation;

the top part of the active substance applicator is inserted positionally correct such onto the bottom part that the circumferentially extending sealing rims are resting on each other;

the top part of the active substance applicator is sealed onto the bottom part at the circumferentially extending sealing rims with counter pressure of the circumferentially extending pressure surface;

the cover element is moved relative to the base element such that the receiving channel formed between them is exposed;

the active substance applicator that is filled and sealed is removed from the receiving element.

According to the solution of the present invention, the filling and closing device has a receiving element for the bottom part of the active substance applicator. The receiving element is provided with a circumferentially extending pressure surface for contacting the support surface of the bottom part as well as with a receiving channel, extending underneath the pressure surface, for the application tube of the bottom part. The receiving element is at least of a two-part configuration with a base element and a cover element that is movable relative to the base element. The receiving channel is formed between the base element and the cover element. The circumferentially extending pressure surface extends across the base element and the cover element in such a way that on the topside of the cover element, which is opposite the receiving channel, a pressure surface section is formed for contacting the support surface section of the active substance applicator that is covered by the application tube.

In the correlated method, the bottom part of the active substance applicator is inserted such into the receiving element that the application tube projects into the receiving channel. The circumferentially extending support surface of the bottom part is thus resting on the circumferentially extending pressure surface in such a way that even the covered support surface section is resting on the pressure surface section of the cover element. In this state, an exact positional fixation of the bottom part in the receiving element is ensured in that, on the one hand, the application tube projects into the receiving channel and is secured thereat. On the other hand, the movable cover element can be moved into the undercut between the application tube and the sealing rim of the bottom part so that, despite this undercut, even at the covered support surface section a support action is achieved by the pressure surface section of the cover element. As a whole, in this way the entire sealing rim of the applicator bottom part is supported along the entire circumferentially extending support surface, which contributes to exact positional fixation. In the subsequent method step, a receiving space bulge of the bottom part that is positionally fixed in the aforementioned way is filled with the active substance preparation.

After filling, the top part of the active substance applicator is placed positionally correct on the bottom part in such a way that the circumferentially extending sealing rims are contacting each other. Subsequently, the top part is sealed onto the bottom part along the circumferentially extending sealing rims with counter pressure of the circumferentially extending pressure surface. In this context, in particular the movable cover element is important which in the aforementioned way projects into the undercut between the application tube and the support surface section that is covered by it and, therefore, despite the application tube positioned underneath, can exert a counter pressure also at this location against the sealing pressure acting from above. Due to the two-part movable configuration, despite the presence of the application tube, a completely closed circumferential pressure surface can be provided which produces an interruption-free circumferentially extending seal-tight sealing seam.

Subsequently, the cover element is moved relative to the base element such that the receiving channel formed between them is open in upward direction. The receiving channel that is now open in upward direction makes it possible that the completed active substance applicator that has been filled and sealed can be lifted by a gripping device in automated fashion in upward direction and removed.

In a preferred further embodiment of the filling and closing device, a concave edge is formed on the active substance applicator between the covered support surface section and the application tube relative to its longitudinal section, wherein on the movable cover element a pressure edge for contacting the aforementioned concave edge of the active substance applicator is formed. Beyond its support and holding action in vertical direction, due to the interaction between the pressure edge of the cover element and the concave edge of the active substance applicator, also a horizontal or laterally acting form-fit positional securing action of the active substance applicator is provided relative to the receiving element.

In an expedient further embodiment, the aforementioned pressure edge of the cover element passes into a holding surface for contacting at least one section of the application tube of the active substance applicator. While the aforementioned circumferentially extending pressure surface supports alone the weight of the applicator blank and optionally also the sealing pressure, the additional holding surface acts in the opposite direction so that the applicator blank cannot carry out easily an upward movement so as to lift off the pressure surface. Accelerations and delays during the course of the entire filling and closing process cannot cause the applicator blank or the completely filled applicator to jump out of its receptacle.

In a preferred embodiment, in the base element, within the circumferentially extending pressure surface, a receptacle for the receiving space bulge of the bottom part of the active substance applicator is formed. On the one hand, this ensures that the applicator bottom part can indeed rest with its sealing rim or its circumferentially extending support surface on the circumferentially extending pressure surface of the receiving element without being lifted by the receiving space bulge. On the other hand, the receptacle, with a geometric adaptation to the receiving space bulge, contributes to the bottom part of the applicator blank being precisely positionally fixed in horizontal or lateral direction with form fit.

It may be expedient to design the cover element relative to the base element so as to be linearly slidable, for example. In a preferred further embodiment, the cover element is pivotable relative to the base element about a pivot axis, wherein the pivot axis is positioned perpendicular relative to the circumferentially extending pressure surface. After completed filling and sealing, the cover element can be pivoted relative to the base element about the aforementioned pivot axis without this causing a height displacement relative to the pressure surface. The active substance applicator maintains during the pivot process its prior existing position and can be easily picked up and vertically lifted by an automated gripping device until the integrally formed application tube is completely lifted out of its receiving channel. The active substance applicator is then no longer in interaction with the receiving element and can be removed by the gripping device as desired.

BRIEF DESCRIPTION OF THE DRAWINGS

One embodiment of the invention will be disclosed in the following with the aid of the drawings in more detail. It is shown in:

FIG. 8 a longitudinal section illustration of a receiving element of the filling and closing device according to FIGS. 4 to 7 with inserted bottom part of the active substance applicator according to FIGS. 1 to 3;

FIG. 9 an enlarged illustration of the detail IX of FIG. 8 with details of the interaction between a cover element of the receiving element and the bottom part of the active substance applicator in the area of its application tube;

FIG. 10 the arrangement according to FIG. 8 when sealing the top part onto the bottom part of the active substance applicator;

FIG. 11 the arrangement according to FIG. 8 through 10 with cover element pivoted into open position for vertical removal of the active substance applicator that is completely filled and sealed.

DESCRIPTION OF PREFERRED EMBODIMENTS

Figure 1:
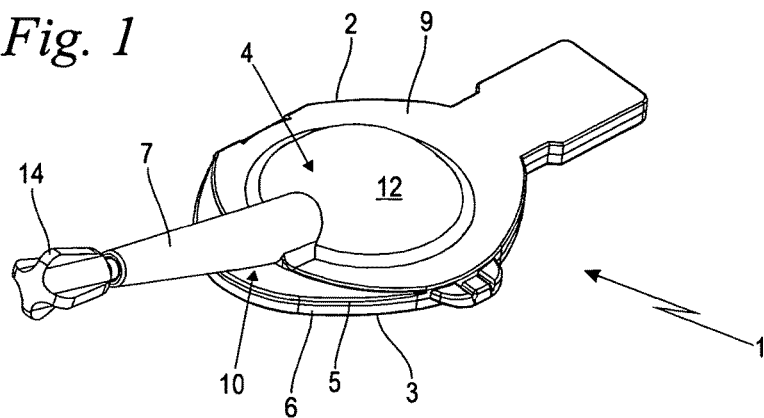
FIG. 1 in a perspective bottom view an active substance applicator for the nose with a projecting application tube.

FIG. 1 shows in a perspective bottom view an active substance applicator 1 for storing a single dosage of an active substance preparation and for administration of this single dosage into the human nose. The active substance applicator 1 comprises a bottom part 2 and a top part 3 between which a receiving space 4 for the aforementioned active substance preparation is formed. For forming the receiving space 4, the bottom part 2 has a receiving space bulge 12 which is surrounded by a sealing rim 5 and which, in the illustrated embodiment, is embodied as a spherical section. Beginning at the receiving space bulge 12, a monolithically formed application tube 7 is extending away which at its free end is closed off by an also monolithically formed closure 14. For use, first the closure 14 is broken off or twisted off and removed. Subsequently, the application tube 7 is introduced into a nostril, wherein then, by pressure applied by finger or thumb onto the receiving space bulge 12, the active substance preparation stored in the receiving space 4 is forced through the application tube 7 into the nose.

The bottom part 2 and the top part 3 each have a sealing rim 5, 6 circumferentially extending about the receiving space 4 by means of which they are seal-tightly connected or sealed with each other. On the bottom part 2 an application tube 7 is monolithically formed which extends, beginning at the receiving space bulge 12 of the bottom part 2, at an acute angle relative to the plane of the sealing rims 5, 6 and thereby extends at least partially, and here completely, across the sealing rim 5 of the bottom part 2 at a spacing thereto. The sealing rim 5 of the bottom part forms on the bottom side, which is facing away from the top part 3 and which, in the illustration according to FIG. 1 is positioned at the top, a circumferentially extending support surface 9. Since the application tube 7 extends at a spacing across the sealing rim 5 and its circumferentially extending support surface 9, a support surface section 10 of the support surface 9 is formed between the application tube 7 and the sealing rim 5 and is covered at least partially by the application tube 7 in the form of an undercut.

Figure 2:
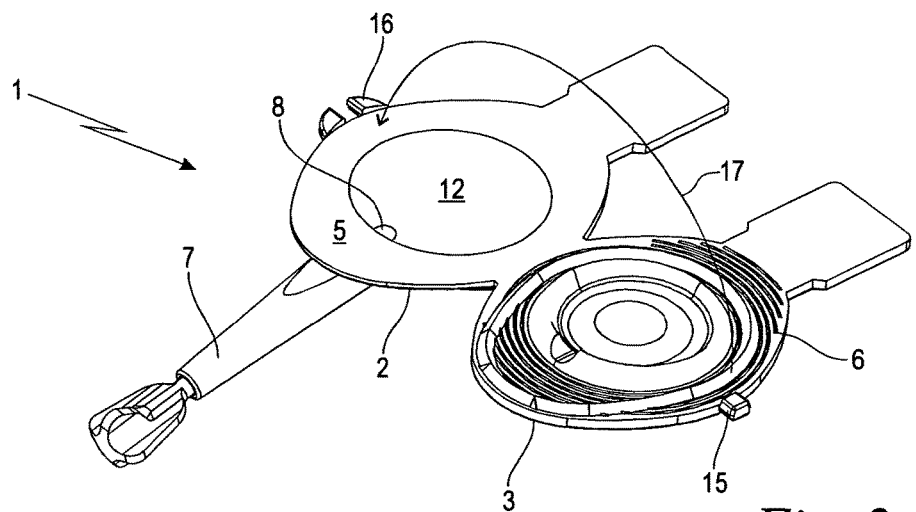
FIG. 2 a plastic blank, folded into open position, for forming the active substance applicator according to FIG. 1 with a bottom part and a top part for illustrating the geometric details.

FIG. 2 shows in a perspective view a plastic blank for forming the active substance applicator 1 according to FIG. 1, wherein in the illustrated plastic blank the bottom part 2 with the application tube 7 and the top part 3 are monolithically produced and connected with each other. However, a two-part configuration with the bottom part 2 and the top part 3 being separate therefrom is also possible. In any case, in the receiving space bulge 12 a mouth 8 is formed by means of which the application tube 7 opens into the receiving space 4 (FIG. 1).

For filling and for closing off the active substance applicator 1, the blank is inserted in its position according to FIG. 2 into the filling and closing device 20 which in the following will be described in connection with FIGS. 4 to 11. The receiving space bulge 12, relative to the direction of the force of gravity, is open in upward direction and can be filled with the active substance preparation. After completion of filling, the top part 3 is folded according to arrow 17 onto the bottom part 2 such that its sealing rim 6 comes to rest on the sealing rim 5 circumferentially extending about the receiving space bulge 12, as is illustrated in the perspective top view of the active substance applicator 1 according to FIG. 3. When looking at FIG. 2 and FIG. 3 together, it is apparent that, when folding into closed position, a locking nose 15 integrally formed on the top part 3 locks in a corresponding locking receptacle 16 of the bottom part 2 and in this way secures the top part 3 in accordance with the illustration of FIG. 3 in its provisionally closed position relative to the bottom part 2. The filled and provisionally closed active substance applicator 1, in the illustration according to FIG. 3, is completely readied for the sealing action that is described in the following in connection with the filling and closing device 20 according to FIGS. 4 to 11.

Figure 3:
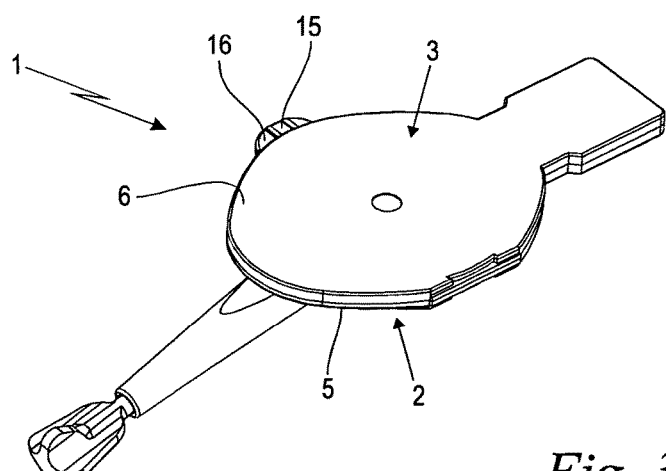
FIG. 3 a perspective top view of the active substance applicator which is formed from the plastic blank according to FIG. 2 with top part that is folded into closed position relative to the bottom part and locked.
Figure 4:
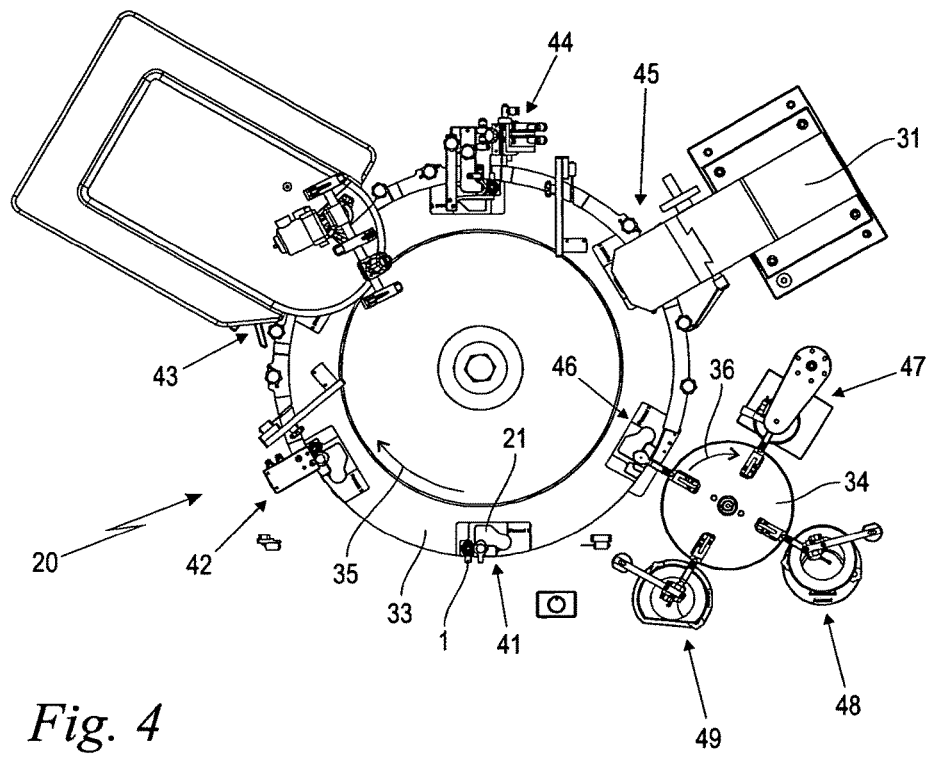
FIG. 4 in a plan view an overview illustration of the filling and closing device according to the invention for the active substance applicator according to FIGS. 1 to 3 with its different stations provided for the method according to the invention.

FIG. 4 shows in a plan view an overview illustration of the filling and closing device 20 according to the invention. The filling and closing device 20 comprises a first larger turntable 33 which in operation is movable in rotation in accordance with arrow 35 as well as a second turntable 34 which in comparison thereto is smaller and is rotatably moved in operation in accordance with arrow 36. The filling and closing device 20 according to the invention is provided for filling and closing the active substance applicator 1 according to FIGS. 1 to 3 or the plastic blank shown therein and forms together therewith a mutually adapted system.

With the two turntables 33, 34, the active substance applicator 1 according to FIGS. 1 to 3 is fed to a total of nine different processing stations. The first turntable 33 is provided for this purpose with a total of six receiving elements 21 distributed about its circumference by means of which, respectively, an active substance applicator 1 or a blank thereof can be supplied to the first six processing stations. A first station 41 serves for inserting the active substance applicator 1 or its unfilled and still open plastic blank. After insertion, it is supplied to a second station 42 for checking its presence and height. Subsequently, a third station 43 for filling the receiving space bulge 12 according to FIG. 2 is accessed. This third station 43 is followed by a fourth station 44 in which the top part 3 is folded onto the bottom part 2 in accordance with the illustration of FIGS. 2 and 3 in order to cause a provisional closing action. In a subsequent fifth station 45, a sealing device 31 is arranged by means of which the top part 3 is sealed onto the bottom part 2 (FIGS. 1 to 3).

In a subsequent sixth station 46, the transfer of the filled and sealed active substance applicator 1 to the second turntable 34 is realized by means of which a seventh station 47 for checking seal-tightness of the active substance applicator 1 is accessed. At an eighth station 48, bad parts are disposed of while in the following ninth and last station 49 the removal of the good parts, i.e., correctly filled and closed, active substance applicators 1 is realized.

Figure 5:
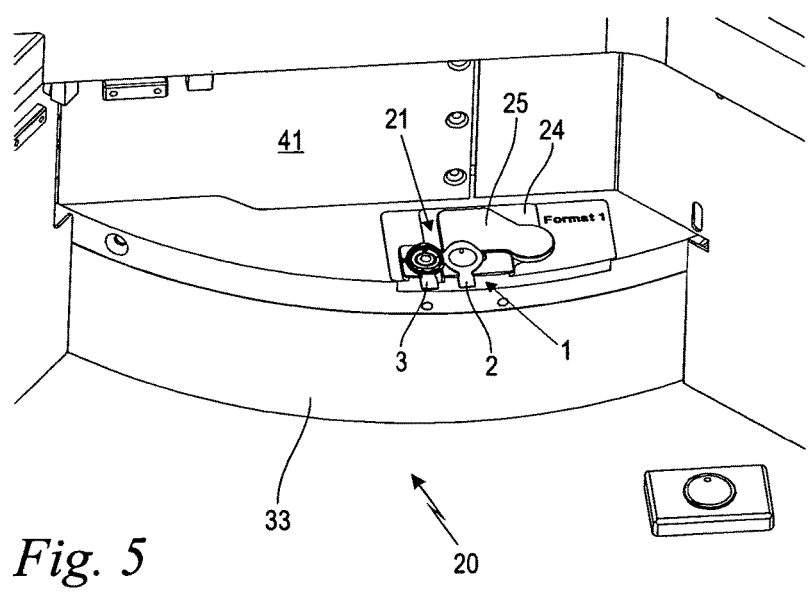
FIG. 5 in a perspective detail view the filling and closing arrangement according to FIG. 4 in the area of its insertion station.

FIG. 5 shows in a perspective detail view the filling and closing device 20 according to FIG. 4 in the area of its first station 41. The illustrated receiving element 21 that is one of a total of six on the first turntable 33 is at least of a two-part configuration and is provided for receiving the open blank of the active substance applicator 1, wherein the receiving element 21 comprises as a first part a base element 24 and as a second part a cover element 25 that is movable relative to the base element 24. Details of the function and mutual interaction between the base element 24, the cover element 25, and the active substance applicator 1 are described in more detail in the following in connection with FIGS. 8 through 11.

In the first station 41, the open plastic blank of the active substance applicator 1 in its configuration according to FIG. 2 is inserted into the receiving element 21 such that both the bottom part 2 and the top part 3 with their future interior side face upwardly relative to the direction of gravity. The insertion of the active substance applicator 1 or its plastic blank is realized in the illustrated embodiment by hand with the cover element 25 closed. An automated insertion with open cover element 25 may be provided also.

Figure 6:
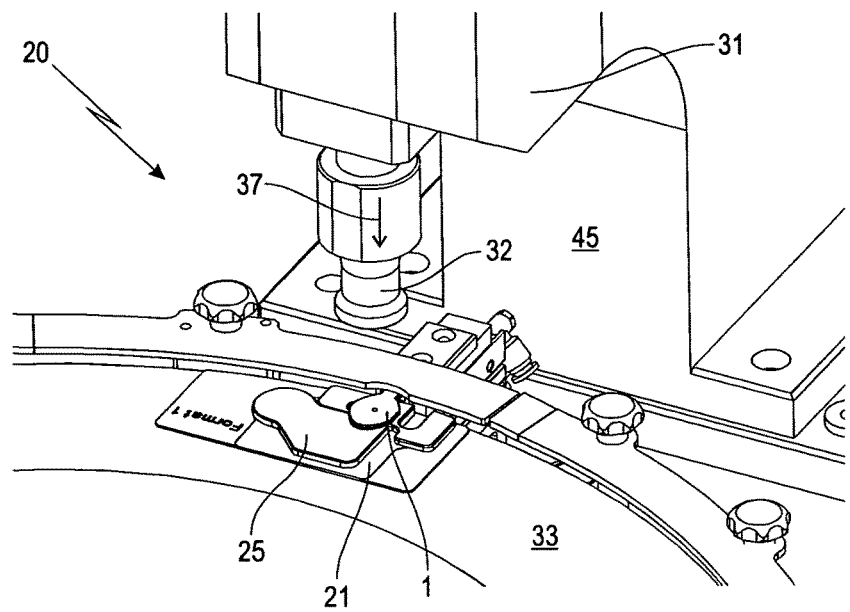
FIG. 6 a perspective detail view of the filling and closing device according to FIG. 4 with details of its sealing station.

FIG. 6 shows in a perspective detail view the filling and closing device 20 according to FIG. 4 in the area of its fifth station 45 with the sealing device 31. With the cover element 25 still closed, the active substance applicator 1 has been filled, already provisionally closed in the configuration according to FIG. 3, and positioned by means of the receiving element 21 on the first turntable 33 below a sealing head 32 of the sealing device 31. The sealing head 32 in the illustrated embodiment is an ultrasonic sealing head and is lowered for sealing in accordance with arrow 37 onto the provisionally closed active substance applicator 1 whereupon then an ultrasonic welding process of the top part 3 with the bottom part 2 (FIGS. 1, 3) is realized.

Figure 7:
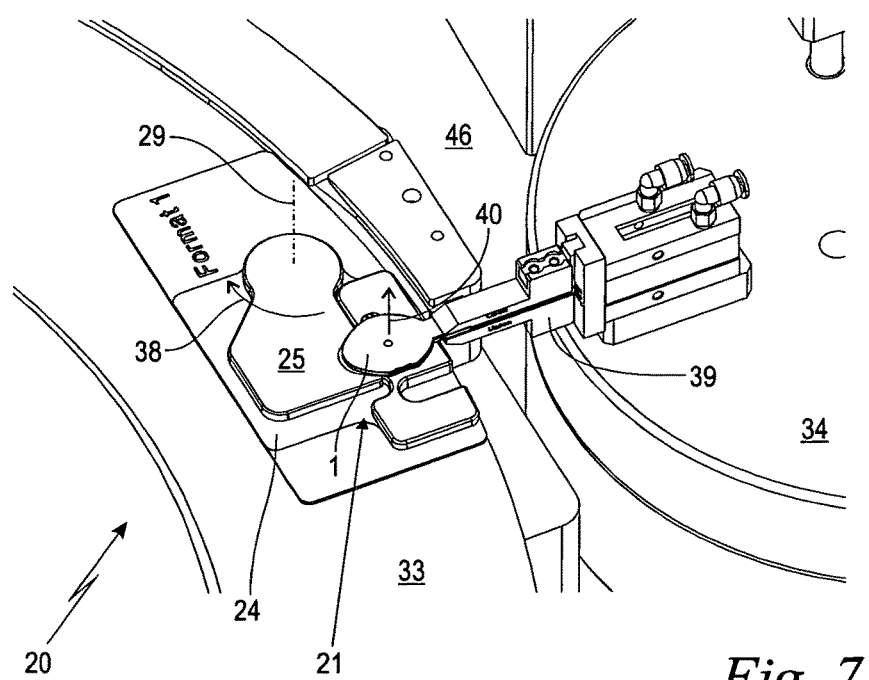
FIG. 7 a perspective detail view of the filling and closing device according to FIG. 4 in the area of its transfer station.

FIG. 7 shows in a perspective detail view the filling and closing device 20 in the area of its sixth station 46 with the completely welded active substance applicator 1 with still closed cover element 25. A gripping device 39 that is mounted on the second turntable 34 grips the active substance applicator 1. The cover element 25 is pivotable relative to the base element 24 about a pivot axis 29 extending in the direction of the force of gravity and is pivoted into open position in accordance with arrow 38, as described in the following in more detail in connection with the FIGS. 8 through 11. In the open pivoted state according to FIG. 11, the active substance applicator 1 is lifted by means of the gripping device 39 in accordance with arrow 40 vertically in upward direction and fed to the downstream seventh, eighth, and ninth stations 47, 48, 49 in accordance with the illustration of FIG. 4.

FIG. 8 shows in a longitudinal section illustration the receiving element 21 according to FIG. 4 with inserted still open blank of the active substance applicator 1 wherein in the illustrated longitudinal section only the bottom part 2 of the active substance applicator 1 with the integrally formed application tube 7 can be seen. In the receiving element 21 a receptacle 30 is formed in which the receiving space bulge 12 of the bottom part 2 is positioned in such a way that the receiving space bulge 12 of the bottom part 2 is arranged such that, in the direction of the force of gravity, the receiving space bulge 12 is open in upward direction and is ready for filling at the third station 43 (FIG. 4). The receptacle 30 is matched with its contour to the contour of the receiving space bulge 12 in such a way that a circumferentially extending edge of the receptacle 30 is resting at the transition area between the receiving space bulge 12 and the adjoining sealing rim 5 and in this way a centering action of the bottom part 2 relative to the receiving element 21 is realized in the horizontal direction.

Moreover, the receiving element 21 has a pressure surface 22 which is extending circumferentially closed about the receptacle 30 and, relative to the direction of the force of gravity, is arranged horizontally and which in its geometric configuration corresponds to the circumferentially extending sealing rim 5 or the support surface 9 (FIG. 1) circumferentially extending thereat. The bottom part 2 is positioned with its circumferentially closed support surface 9 flat on the also closed circumferentially closed pressure surface 22.

In the receiving element 21 a receiving channel 23 is formed which, beginning at the receptacle 30, extends laterally below and past the support surface 9 and is formed between the base element 24 and the cover element 25. For this purpose, in the base element 24 an upwardly open channel is formed which is matched in its shape to the shape of the application tube and which in upward direction is closed or covered by the closed cover element 25. The closed receiving channel 23 is therefore delimited by the channel walls formed in the base element 24 and is delimited in upward direction by the cover element 25 and receives the application tube 7 of the bottom part 2.

FIG. 9 shows the enlarged detail IX according to FIG. 8 in the area of the cover element 25, the sealing rim 5, and the application tube 7. It can be seen that, in the illustrated longitudinal section, the application tube 7 extends across the sealing rim 5 of the bottom part 2 relative to its plane at least partially, here completely, in such a way that an undercut is formed between the support surface 9 and the application tube 7 relative to the vertical direction. In the area of this undercut, the circumferentially extending support surface 9 has a support surface section 10 which, in vertical direction downwardly, is covered at least partially, here completely, by the application tube 7 that is extending underneath at a spacing thereto.

When looking at both FIGS. 8 and 9, it is apparent that the circumferentially extending pressure surface 22 extends across the top side of the base element 24 as well as across the top side of the cover element 25. In this context, in the area of the covered support surface section 10, a pressure surface section 26 of the pressure surface 22 is formed at the cover element 25 on its topside that is opposite the receiving channel 23; the support surface section 10 of the support surface 9 is resting thereon. Despite the bottom side coverage of the support surface 9 in the support surface section 10 by the application tube 7, the support surface 9 as a whole, i.e., including its covered support surface section 10, experiences a vertical, circumferentially closed support action against the pressure from above that is occurring during the sealing process according to FIGS. 6 and 10.

The detail view according to FIG. 9 also shows that at the active substance applicator 1, relative to its longitudinal section cutting through the bottom part 2 with the application tube 7, a concave edge 11 is formed between the covered support surface section 10 and the application tube 7. The movable cover element 25 is provided with a convex pressure edge 27 which is facing in the direction of this concave edge 11 and which delimits the pressure surface section 26 inwardly relative to the receptacle 30, on which the bottom part 2 of the active substance applicator 1 is resting with its concave edge 11 in the inserted state. Relative to the illustrated longitudinal section, the pressure edge 27 of the cover element 25, beginning at the upper pressure surface section 26, passes in downward direction into a holding surface 28 which, in vertical direction, is facing away from the pressure surface section 26, on which at least one section of the application tube 7 of the active substance applicator 1 is resting in the inserted state. As a whole, the cover element 25 with its pressure edge 27, the upper pressure surface section 26, and the lower holding surface 28 therefore projects into the intermediate space between the application tube 7 and the sealing rim 5 so that the bottom part 2 in vertical direction upwardly, downwardly as well as laterally in horizontal direction is secured relative to the receiving element 21.

FIG. 10 shows the arrangement according to FIG. 8, wherein the top part 3, not illustrated in FIG. 8, in accordance with the illustration of FIG. 3 has been folded onto the bottom part 2 of the active substance applicator 1 after the previously upwardly open receiving space bulge 12 has been filled in the configuration according to FIG. 8 in the third station 43 (FIG. 4) with the active substance preparation. In the fifth station 45 (FIGS. 4, 6) in accordance with the illustration of FIG. 10, the sealing head 32 in accordance with arrow 37 is now lowered and is pressed onto the upper sealing rim 6 of the top part 3 that is resting on top. The counter pressure which is maintaining a balance to the pressure that is acting in the direction of arrow 37 is generated by the circumferentially extending pressure surface 22 at the also circumferentially extending support surface 9; this includes the pressure surface section 26 at the covered support surface section 10. The sealing head 32 has a circumferentially extending sealing edge whose contour corresponds to the circumferentially extending contour of the sealing rims 5, 6 so that here an ultrasonic welding of the top part 3 with the bottom part 2 is realized with formation of the filled and hermetically closed receiving space 4.

After sealing or after ultrasonic welding, the receiving element 21 with the active substance applicator 1 secured therein is then moved in accordance with the illustration of FIGS. 4, 7 by means of the first turntable 33 to the sixth station 46 where removal of the active substance applicator 1 from the receiving element 41 by means of the gripping device 39 is to be realized. This situation is illustrated in detail in FIG. 11 wherein the arrangement according to FIG. 8 with cover element 25 that is pivoted into open position relative to the base element 24 of the receiving element 21 is illustrated. It can be seen that the vertical pivot axis 29 is positioned perpendicularly relative to the circumferentially extending pressure surface 22. In particular when looking at both FIGS. 9 and 11, it is apparent that due to the vertical position of the pivot axis 29 the cover element 25 can be moved out of the undercut area between the covered support surface section 10 and the application tube 7 of the active substance applicator 1 without this causing a positional change or a lifting action of the active substance applicator 1. According to the illustration of FIG. 11, the cover element 25 is pivoted to such an extent into open position that the receiving channel 23, relative to the horizontally projected length of the application tube 7, is completely open in upward direction. This makes it possible, as can be seen when looking at both FIGS. 7 and 11, to remove the completely filled and sealed active substance applicator 1 by means of the gripping device 39 in automated fashion in upward direction in the direction of arrow 40 and completely remove it from the receiving element 21 without the application tube 7 colliding with the cover element 25.

It has been mentioned initially that the open blank of the active substance applicator 1 in accordance with the illustration of FIG. 5 can be inserted manually into the receiving element 21 with closed cover element 25. This is done in that the blank of the active substance applicator 1 in accordance with the illustration of FIG. 8 is inserted at least approximately in longitudinal direction of the application tube 7 manually into the receiving channel 23 and is then pressed with the receiving space bulge 12 into the receptacle 30. This complex movement process requires manual handling. However, in analogy to the illustration of FIG. 11, an automated insertion of the applicator blank opposite to arrow 40 from top to bottom by means of a suitable gripping device or the like can be expedient wherein then the cover element 25 is first open in accordance with the illustration of FIG. 11 and only subsequently is pivoted into the position 8, 9.

What is claimed is:

1. A filling and closing device for an active substance applicator, wherein the active substance applicator comprises a bottom part and a top part and a receiving space for an active substance preparation defined between the bottom part and the top part, wherein the bottom part and the top part each have a circumferentially extending sealing rim adapted to generate a seal-tight connection between the top part and the bottom part, wherein the bottom part is provided with an application tube with an inner mouth that opens into the receiving space, wherein the sealing rim of the bottom part has a bottom side facing away from the top part and the bottom side forms a circumferentially extending support surface, wherein the application tube extends across the bottom side such that the circumferentially extending support surface has a covered support surface section that is at least partially covered by the application tube, wherein the filling and closing device comprises:

a receiving element adapted to receive the bottom part of the active substance applicator;

wherein the receiving element comprises a circumferentially extending pressure surface adapted to contact the circumferentially extending support surface of the bottom part;

wherein the receiving element further comprises a receiving channel adapted to receive the application tube, wherein the receiving channel extends underneath the circumferentially extending pressure surface;

wherein the receiving element is of an at least two-part configuration comprising a base element and a cover element, wherein the cover element is movable relative to the base element;

wherein the receiving channel is formed between the base element and the cover element;

wherein the circumferentially extending pressure surface extends across the base element and the cover element;

wherein the circumferentially extending pressure surface has a pressure surface section provided on a topside of the cover element, the topside arranged so as to face away from the receiving channel;

wherein the pressure surface section is adapted to contact the covered support surface section of the active substance applicator.

2. The filling and closing device according to claim 1, wherein the cover element comprises a pressure edge adapted to contact a concave edge of the active substance applicator, the concave edge, viewed in a longitudinal section view of the active substance applicator, arranged between the covered support surface section and the application tube.

3. The filling and closing device according to claim 2, wherein the pressure edge of the cover element passes into a holding surface of the cover element, wherein the holding surface is adapted to contact at least one section of the application tube.

4. The filling and closing device according to claim 1, wherein the base element has a receptacle within the circumferentially extending pressure surface, the receptacle adapted to receive a receiving space bulge of the bottom part.

5. The filling and closing device according to claim 1, wherein the cover element is pivotable relative to the base element about a pivot axis, wherein the pivot axis is perpendicular relative to the circumferentially extending pressure surface.

6. The filling and closing device according to claim 1, further comprising a sealing device with a sealing head, wherein the sealing head has a shape matching a shape of the circumferentially extending sealing rims and a shape of the circumferentially extending pressure surface, wherein the sealing head is adapted to be lowered from a raised position onto the circumferentially extending pressure surface of the receiving element with the sealing rims positioned between the sealing head and the circumferentially extending pressure surface.

7. The filling and closing device according to claim 6, wherein the sealing device is an ultrasonic welding device.

8. A method for filling and closing an active substance applicator with a filling and closing device according to claim 1, the method comprising:

inserting the bottom part of the active substance applicator into the receiving element of the filling and closing device such that the application tube projects into the receiving channel, the circumferentially extending support surface is resting on the circumferentially extending pressure surface, and the covered support surface section is resting on the pressure surface section;

filling a receiving space bulge of the bottom part of the active substance applicator with an active substance preparation;

positioning the top part of the active substance applicator positionally correct on the bottom part such that the circumferentially extending sealing rims of the bottom part and the top part are resting on each other;

sealing the top part of the active substance applicator onto the bottom part along the circumferentially extending sealing rims and applying counter pressure with the circumferentially extending pressure surface during sealing;

exposing the receiving channel by moving the cover element relative to the base element;

removing the active substance applicator, which is filled and sealed, from the receiving element.

9. The method according to claim 8, further comprising:

in the step of exposing, pivoting the cover element relative to the base element about a pivot axis that is perpendicular to the circumferentially extending pressure surface; and in the step of removing, vertically lifting the active substance applicator out of the receiving element.

* * * * *